US010302554B2

(12) United States Patent
Tumpold et al.

(10) Patent No.: US 10,302,554 B2
(45) Date of Patent: May 28, 2019

(54) ACOUSTIC WAVE DETECTOR

(71) Applicant: Infineon Technologies AG, Neubiberg (DE)

(72) Inventors: David Tumpold, Kirchheim (DE); Alfons Dehe, Reutlingen (DE); Christoph Glacer, Munich (DE)

(73) Assignee: Ingineon Technologies AG, Neubiberg (DE)

( * ) Notice: Subject to any disclaimer, the term of this patent is extended or adjusted under 35 U.S.C. 154(b) by 230 days.

(21) Appl. No.: 15/172,178

(22) Filed: Jun. 3, 2016

(65) Prior Publication Data

US 2017/0350810 A1  Dec. 7, 2017

(51) Int. Cl.
*G01N 21/17* (2006.01)

(52) U.S. Cl.
CPC . *G01N 21/1702* (2013.01); *G01N 2021/1704* (2013.01)

(58) Field of Classification Search
CPC .......... G01N 21/3504; G01N 21/1704; G01N 21/1702; G01N 2021/1708; G01N 29/2418; G01N 2021/1704; A61B 5/0095
USPC .... 73/24.02, 643; 356/437, 4.01, 5.01, 5.03; 367/13, 21
See application file for complete search history.

(56) References Cited

U.S. PATENT DOCUMENTS

| | | | | |
|---|---|---|---|---|
| 6,082,178 A | * | 7/2000 | Bernstein | G01N 21/1702 73/24.02 |
| 2008/0011055 A1 | * | 1/2008 | Riddle | G01N 21/1702 73/24.02 |
| 2008/0252891 A1 | * | 10/2008 | Uber | G01N 21/1702 356/437 |
| 2011/0147592 A1 | | 6/2011 | Martin | |

(Continued)

FOREIGN PATENT DOCUMENTS

| | | |
|---|---|---|
| DE | 10303263 B4 | 1/2012 |
| KR | 2006-0043413 A | 5/2006 |

(Continued)

OTHER PUBLICATIONS

Korean Office Action based on Application No. 2017-0068419 (5 pages) dated Jul. 19, 2018 (for reference purpose only).

(Continued)

*Primary Examiner* — Lisa M Caputo
*Assistant Examiner* — Irving A Campbell
(74) *Attorney, Agent, or Firm* — Viering, Jentschura & Partner MBB

(57) ABSTRACT

An acoustic wave detector may include: an exterior housing with an exterior housing wall, a gas chamber located within the exterior housing and configured to receive a gas therein. The exterior housing wall may include an aperture providing a gas passage between the gas chamber and the exterior of the acoustic wave detector. The acoustic wave detector may further include an excitation element configured to selectively excite gas molecules of a specific type in the gas (Continued)

received in the gas chamber in a time-varying fashion, thereby generating acoustic waves in the gas, and an acoustic wave sensor configured to detect the acoustic waves generated in the gas and acoustic waves generated outside of the acoustic wave detector. The acoustic wave sensor may have an acoustic port overlapping with the aperture in the exterior housing wall.

23 Claims, 7 Drawing Sheets

(56) References Cited

U.S. PATENT DOCUMENTS

| | | | |
|---|---|---|---|
| 2011/0296900 A1 | 12/2011 | Thorson | |
| 2012/0247183 A1* | 10/2012 | Rezachek | G01N 21/1702 73/24.02 |
| 2013/0027707 A1* | 1/2013 | Matsushita | G02B 26/001 356/432 |
| 2015/0101395 A1 | 4/2015 | Dehe et al. | |

FOREIGN PATENT DOCUMENTS

| | | |
|---|---|---|
| KR | 1020110059608 A | 6/2011 |
| KR | 2011-0132982 A | 12/2011 |

OTHER PUBLICATIONS

Decision to Grant received for the corresponding Korean Patent Application No. 2017-0068419 (2 pages) dated Mar. 20, 2019 (for reference purpose only).

\* cited by examiner

ACOUSTIC WAVE DETECTOR

TECHNICAL FIELD

Various embodiments relate generally to an acoustic wave detector.

BACKGROUND

Acoustic wave detectors have gained significant importance in modern life, either as part of a voice transmission device or of a photoacoustic detector employed in a gas analyzer for analyzing gases such as ambient air. Since the analysis of the composition of ambient air, e.g. due to pollution, is becoming increasingly important, it is desirable to provide a compact acoustic wave detector that is flexible at use.

SUMMARY

According to various embodiments, an acoustic wave detector is provided. The acoustic wave detector may include: an exterior housing with an exterior housing wall, a gas chamber located within the exterior housing and configured to receive a gas therein. The exterior housing wall may include an aperture providing a gas passage between the gas chamber and the exterior of the acoustic wave detector. The acoustic wave detector may further include an excitation element configured to selectively excite gas molecules of a specific type in the gas received in the gas chamber in a time-varying fashion, thereby generating acoustic waves in the gas, and an acoustic wave sensor configured to detect the acoustic waves generated in the gas and acoustic waves generated outside of the acoustic wave detector. The acoustic wave sensor may have an acoustic port overlapping with the aperture in the exterior housing wall.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

Figure 1:
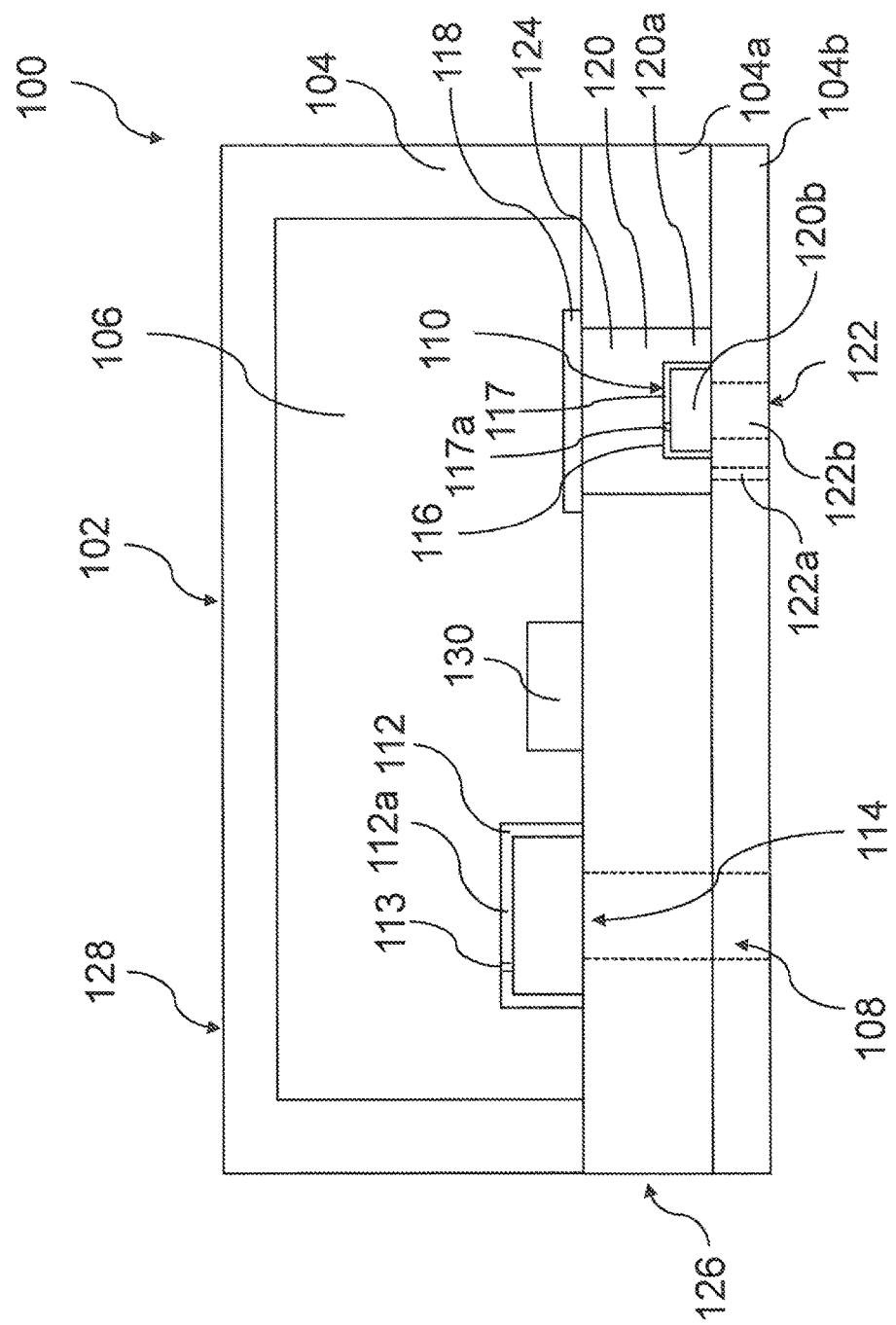
FIG. 1 shows a schematic view of an exemplary acoustic wave detector.

FIG. 1 shows an acoustic wave detector 100 including an exterior housing 102 with an exterior housing wall 104 and a gas chamber 106 located within the exterior housing 102 and configured to receive a gas therein. The exterior housing wall 104 may include an aperture 108 providing a gas passage between the gas chamber 106 and the exterior of the acoustic wave detector 100.

The term "exterior housing wall" used throughout this specification denotes an outer periphery of the acoustic wave detector 100 that is not covered by other housing parts, i.e. it defines an outer boundary of the acoustic wave detector 100.

The acoustic wave detector 100 may further include an excitation element 110 configured to selectively excite gas molecules of a specific type in the gas received in the gas chamber 106 in a time-varying fashion. The excitation element 110 may be configured to induce a specific atomic or molecular excitation of a gas molecule in the gas to be analyzed and/or to excite various vibrational and/or rotational modes of said gas molecules. This excitation causes a positive pressure pulse.

Switching off the excitation source causes the excited gas molecules to relax and give a negative pressure pulse. Since the specific gas molecules to be analyzed are excited in a time-varying fashion, e.g. periodically, a time-varying, e.g. a periodic, pressure fluctuation is generated in the gas to be analyzed. More specifically, acoustic waves are generated that are indicative of the content of the gas molecules of a specific type in the gas. The concentration of the gas molecules in the gas is proportional to the generated sound pressure.

The acoustic wave detector 100 may be used for monitoring the composition of ambient air, e.g. for a detection of the content of $CO_2$ in ambient air and/or for detecting toxic gases such as CO in ambient air. Methane and/or water molecules (humidity) in ambient air may also be detected in this way. Alternatively or additionally, the acoustic wave detector 100 may be configured and used as a breathalyzer to measure the content of alcohol and/or acetone which is indicative of the blood glucose level.

As shown in FIG. 1, the acoustic wave detector 100 may include an acoustic wave sensor 112 configured to detect the acoustic waves generated in the gas and acoustic waves generated outside of the acoustic wave detector 100. A way of discriminating the acoustic waves generated in the gas by the excitation element 110 from acoustic waves generated outside of the acoustic wave detector 100 will be discussed later when describing the working principle of the excitation element 110 in greater detail.

The acoustic wave sensor 112 may have a membrane 112a displaceable by the acoustic waves to be detected. A displacement of the membrane 112a may be indicative of characteristics of the acoustic waves to be detected such as of the frequency and/or intensity of the acoustic waves.

The membrane 112a may be positioned in a paralled relationship to a fixed reference membrane defining therewith a capacitor the capacitance of which may be alterable by a displacement of the membrane 112a. Consequently, by measuring this capacitance, a signal indicative of the characteristics of the acoustic waves can be obtained. Alternatively or additionally a piezoelement may be used to sense a displacement of the membrane 112a.

As shown in FIG. 1, the membrane 112a of the acoustic wave sensor 112 may delimit the gas chamber 106 in order to efficiently detect acoustic waves generated therein. The membrane 112a may include at least one opening 113 formed therethrough providing a gas inlet and/or a gas outlet of the gas chamber 106.

The at least one opening 113 may have a diameter in the range from about 10 μm to about 50 μm. In various embodiments, the membrane 112a may have an opening 113 with a diameter of about 30 μm. To provide a sufficient flow area in the membrane 112a, a plurality of openings, e.g. 30 openings, may be formed therethrough. In this way, a gas between the gas chamber 106 and the exterior of the acoustic wave detector 100 may be exchanged by diffusion through the aperture 108 provided in the exterior housing wall 104 and the openings 113 provided in the membrane 112a of the acoustic wave sensor 112. The diffusion time associated with a gas chamber 106 with a volume of about 1 $mm^3$ may amount to about 1 minute. Gas chambers 106 with larger volumes of up to 10 $mm^3$ are also conceivable.

As shown in FIG. 1, the acoustic wave sensor 112 may include an acoustic port 114 overlapping with the aperture 108 in the exterior housing wall 104. In this way, acoustic waves to be detected from outside of the acoustic wave detector 100 are efficiently supplied to the acoustic wave sensor 112. In the exemplary acoustic wave detector 100 as shown in FIG. 1, the membrane 112a may overlap with the aperture 108 provided in the exterior housing wall 104. In this way, acoustic waves entering the acoustic wave sensor 112 are efficiently directed to the membrane 112a, thereby providing a highly efficient detection of acoustic waves from the outside of the acoustic wave detector 100.

In this exemplary acoustic wave detector 100, the acoustic wave sensor 112 forms a part of the gas passage connecting the gas chamber 106 with the exterior of the acoustic wave detector 100. Furthermore, the gas chamber 106 is in permanent gas flow communication with the exterior of the acoustic wave detector 100. In this way, changes of the composition of, e.g., of ambient air may be quickly detected.

The acoustic wave detector 100 may be mounted in a mobile device such as in a mobile phone. In this way, the acoustic wave detector 100 may be flexibly utilized. In this case the acoustic wave sensor 112 may be configured as a microphone, such as a MEMS microphone, and the gas chamber 106 may be part of the backvolume of the microphone. In this way, a phone with a compact structure can be provided.

The excitation element 110 may include a radiation source 116 configured to emit radiation into the gas chamber 106. The radiation may be suitable to selectively excite gas molecules of a specific type in the gas in a time-varying fashion, thereby generating acoustic waves.

The radiation source 116 may be configured to emit electromagnetic radiation in the infrared and/or in the visible and/or in the ultraviolet frequency range. Infrared light is suitable for exciting vibrational molecular modes. By way of example, infrared light with a wavelength of about 4.25 μm is suitable for exciting vibrational modes of $CO_2$.

The radiation source 116 may be configured to emit light pulses at predetermined time intervals, e.g. periodically. The time intervals at which the pulses are emitted by the radiation source 116 may determine the frequency of the acoustic waves induced in the gas provided that the relaxation of the gas occurs on a time scale that is shorter than the time difference between two immediately consecutive light pulses emitted by the radiation source 116.

In an exemplary acoustic wave detector 100, light pulses may be emitted at time intervals in the range from about 0.01 s to about 0.1 s inducing acoustic waves with a frequency of about 10 Hz to about 100 Hz, i.e. with an acoustic frequency in the low-frequency regime of the audible frequency range from about 20 Hz to 20 kHz.

Consequently, the thus induced acoustic waves are hardy perceptible by humans. Therefore, in case the acoustic wave detector is mounted in a mobile phone, the acoustic wave detector 100 may be permanently operated, i.e. even during telephone calls, without significantly deteriorating the speech quality. Alternatively, the operation of an acoustic wave detector 100 mounted in a mobile phone may of course be interrupted during a telephone call.

Since the frequency of the acoustic waves induced by the radiation source 116 in the gas is fixed due to the frequency of the excitation pulses, acoustic waves generated in the gas by the excitation element 110 can be efficiently discriminated from acoustic waves generated outside of the acoustic wave detector 100 that do not have a well-defined fixed frequency. In addition, the acoustic wave detector 100 may employ a lock-in discrimination scheme based on the time correlation between the operation of the excitation element 110 and the detection of acoustic waves of the predetermined frequency.

The radiation source 116 may include at least one of a group consisting of a black body, a photodiode and a laser. A black body emits radiation according to Planck's law, meaning that the spectrum emitted by it is determined by its temperature, not by its shape or composition.

The black body may be configured as an electrically heatable membrane. The membrane may be heated up to several hundreds of degrees Celcius, e.g. to about 600° C. in operation.

For a selective excitation of only a single type of gas molecules present in the gas to be analyzed, it may be necessary to limit the radiation spectrum of the radiation source 116 to a narrow energy band to make sure that gas molecules of another type are not unintentionally also excited which may deteriorate the measurement accuracy.

Radiation with a well-defined energy may be provided by a filter 118 configured to selectively transmit radiation of a predetermined energy emitted by the radiation source 116 into the gas chamber 106. The filter 118 may also be configured to thermally insulate the excitation source 110 from the gas chamber 106 to avoid a thermoacoustic effect that may overdrive the photo acoustic signal. A thermal insulation between the mounting portion of the excitation source 110 and the gas chamber 106 may be provided irrespective of whether a filter is required or not. This means that a thermally insulating window may be provided that is not configured as a filter.

In case only a single type of gas molecules is to be detected in the gas to be analyzed, a filter 118 with fixed transmission characteriscs, i.e. a fixed transmission band of a fixed wavelength, can be used. Alternatively, in case gas molecules of different types having different excitation energies are to be detected in the gas, a tunable filter 118 may be employed the transmission characteristics of which are tunable. In operation, the transmission characteristics can be varied in a time-varying fashion, e.g. periodically, to individually excite the types of gas molecules of interest.

The fixed or tunable filter 118 may include at least one of a plasmonic filter or a Fabry-Pérot interferometer.

As shown in FIG. 1, the filter 118 may partition the interior of the acoustic wave detector 100 into the gas chamber 106 and a radiation source chamber 120 housing the radiation source 116.

The radiation source chamber 120 may be partly delimited by the exterior housing wall 104 of the exterior housing 102. In order to dissipate heat generated by the radiation source 116 in operation and to release the pressure generated as a direct result thereof, e.g. if the radiation source 116 includes an electrically heatable membrane, the exterior housing wall 104 may include a heat-exchange or pressure-compensation passage 122 between the radiation source chamber 120 and the exterior of the acoustic wave detector 100. In this way, a temperature rise, e.g. of the gas in the gas chamber 106, may be avoided, that may otherwise deteriorate the measurement accuracy.

In case the radiation source 116 includes an electrically heatable membrane 117, the membrane 117 may partition the radiation source chamber 120 into first and second sub-chambers 120a, 120b. In this configuration, the exterior housing wall 104 may include first and second heat-exchange or pressure-compensation passages 122a, 122b between the first and second sub-chambers 120a, 120b, respectively, and the exterior of the acoustic wave detector 100. In this way, differential pressures generated by the radiation source 116 can be efficiently compensated. An efficient pressure-compensation may be additionally or alternatively provided by a pressure-compensation hole 117a in the membrane 117.

As shown in FIG. 1, the radiation source chamber 120 may be formed in a recess 124 provided in the exterior housing wall 104 that is covered by the window (filter) 118. In this way, a gas chamber 106 with a large volume can be provided.

The filter 118 may gastightly cover the recess 124 in the exterior housing wall 104 to avoid an undefined gas flow into the radiation source chamber 120.

The recess 124 may be formed in a portion of the exterior housing wall 104 that includes a plurality of housing-wall layers 104a, 104b. As shown in FIG. 1, the radiation source 116 may be supported on a housing-wall layer 104b different from an inner housing-wall layer 104a forming part of an inner surface of the exterior housing wall 104, e.g., on a housing-wall layer 104b forming part of an outer surface of the exterior housing wall 104. This configuration provides a way of thermally decoupling the radiation source 116 from the gas received in the gas chamber 106, e.g. by providing a thermally insulating film between the housing-wall layer 104b supporting the radiation source 116 and the inner housing-wall layer 104a.

Alternatively or additionally, the housing-wall layer 104b on which the radiation source is supported may have a lower thermal conductivity than the inner housing-wall layer 104a. The outer housing-wall layer 104b may be made of a material having a thermal conductivity of less than about 10 W/(m·K) or even less than about 5 W/(m·K).

The exterior housing wall 104 may include a substrate 126 and a lid 128 defining the gas chamber 106 therebetween. The gas chamber 106 may be delimited by the substrate 126 and the lid 128, as shown in FIG. 1.

The substrate 126 may be made at least in part of a semiconductor such as silicon. The lid 128 may be made of a material with a high thermal conductivity such as of a metal to provide a highly conductive thermal link to a heat sink outside of the acoustic wave detector 100. A holder of the acoustic wave detector 100 or a person carrying the acoustic wave detector 100 may act as a heat sink.

In an exemplary acoustic wave detector 100, the acoustic wave sensor 112 and the excitation element 110 may be mounted on the substrate 126, e.g. on a side of the substrate 126 facing towards the interior of the exterior housing 102.

As shown in FIG. 1, also an electronic component 130 may be mounted on the substrate 126. The electronic component 130 may be configured to control the radiation source 116, e.g. the time intervals at which radiation pulses are emitted as well as the duration of the individual radiation pulses. The electronic component 130 may be also configured to control the transmission characteristics of a tunable filter 118.

The electronic component 130 may be additionally or alternatively configured to analyze signals output from the acoustic wave sensor 112 in order to determine the content of gas molecules of a specific type in the gas from a signal output by the acoustic wave sensor 112. In various embodiments, it may be configured to discriminate signals induced in the acoustic wave sensor 112 by acoustic waves generated in the gas chamber 106 from signals induced in the acoustic wave sensor 112 by acoustic waves generated outside of the acoustic wave detector 100. In an exemplary acoustic wave detector 100, the electronic component 130 may be configured as an application specific integrated circuit (ASIC).

In order to provide a highly efficient excitation of gas molecules to be detected in the gas, the gas chamber 106 may be delimited by a reflector. In an exemplary device, the interior surface of the exterior housing 104 may be formed at least in part of a material having a high reflectivity in the frequency range of the emitted electromagnetic radiation. In the acoustic wave sensor 100 shown in FIG. 1, the inner surfaces of the substrate 126 and/or the lid 128 delimiting the gas chamber 106 may be configured as reflectors.

The reflector delimiting the gas chamber 106 may have a reflectance in the infrared and/or in the visible and/or in the ultraviolet frequency range of at least 20% or, of at least 50% or even of at least 80%.

Figure 2:
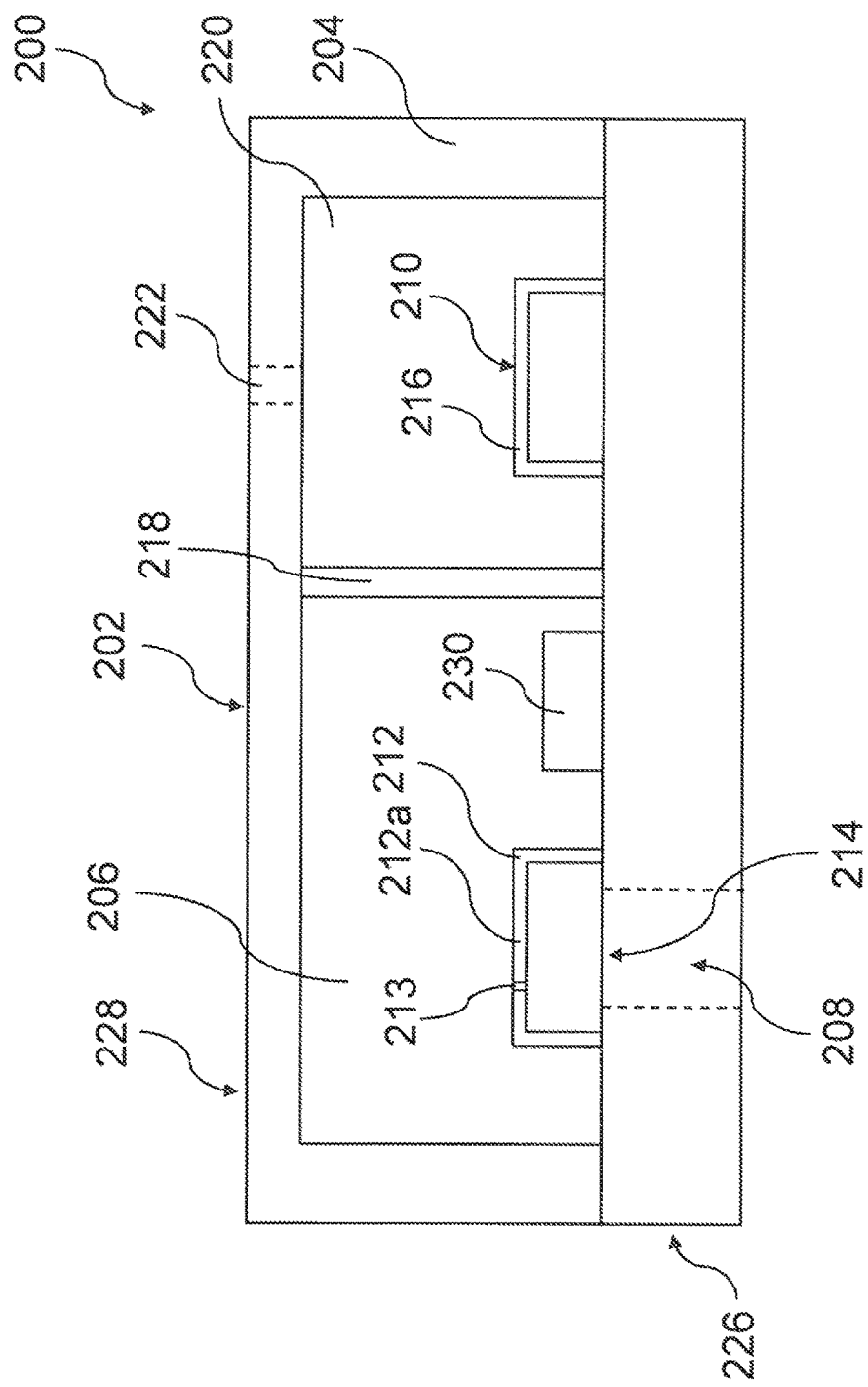
FIG. 2 shows a schematic view of a modified acoustic wave detector.

FIG. 2 shows a schematic view of a modified acoustic wave detector 200. In FIG. 2, elements corresponding to elements of the acoustic wave detector 100 shown in FIG. 1 are denoted by the same reference numerals, however enhanced by the number 100. The acoustic wave detector 200 shown in FIG. 2 will be described only inasmuch as it differs from the acoustic wave detector 100 shown in FIG. 1.

The acoustic wave detector 200 shown in FIG. 2 includes a radiation source 216, that, different from the acoustic wave detector 100 shown in FIG. 1, is not located within a recess provided in the exterior housing wall 204. Instead, the radiation source 216 is mounted on a basically plane portion of the interior surface of the exterior housing wall 204. The exterior housing wall 204 includes, similar to the exterior housing wall 104 of the acoustic wave detector 100 shown in FIG. 1, a substrate 226 and a lid 228. The radiation source 216 is mounted on the substrate 226.

The acoustic wave detector 200 includes a (radiation window and/or) filter 218 that partitions the interior of the exterior housing 202 into a gas chamber 206 and into a radiation source chamber 220. The filter 218 may be positioned between two opposing parts of the inner surface of the exterior housing wall 204, e.g. between inner surfaces of the lid 228 and of the substrate 226. The filter 218 may be in physical contact along its entire circumference with the interior surface of the exterior housing wall 204 and may gastightly separate the gas chamber 206 from the radiation source chamber 220.

To efficiently compensate thermoacoustic pressure differences generated by the radiation source 216, a heat-exchange or pressure-compensation passage 222 may be provided in a part of the exterior housing wall 204 delimiting the radiation source chamber 220, e.g. in the lid 228.

The radiation source chamber 220 may of course be provided with a plurality of heat-exchange or pressure-compensation passages, e.g. in case the radiation source 216 is configured as an electrically heatable membrane that partitions the radiation source chamber 220 into a plurality of sub-chambers. In this case, similar to the acoustic wave detector 100 shown in FIG. 1, for each sub-chamber an individual pressure-compensation passage may be provided in the exterior housing wall 204.

The other principles of the present invention explained with respect to the acoustic wave detector 100 shown in FIG. 1 apply accordingly also to the acoustic wave detector 200 shown in FIG. 2.

Figure 3:
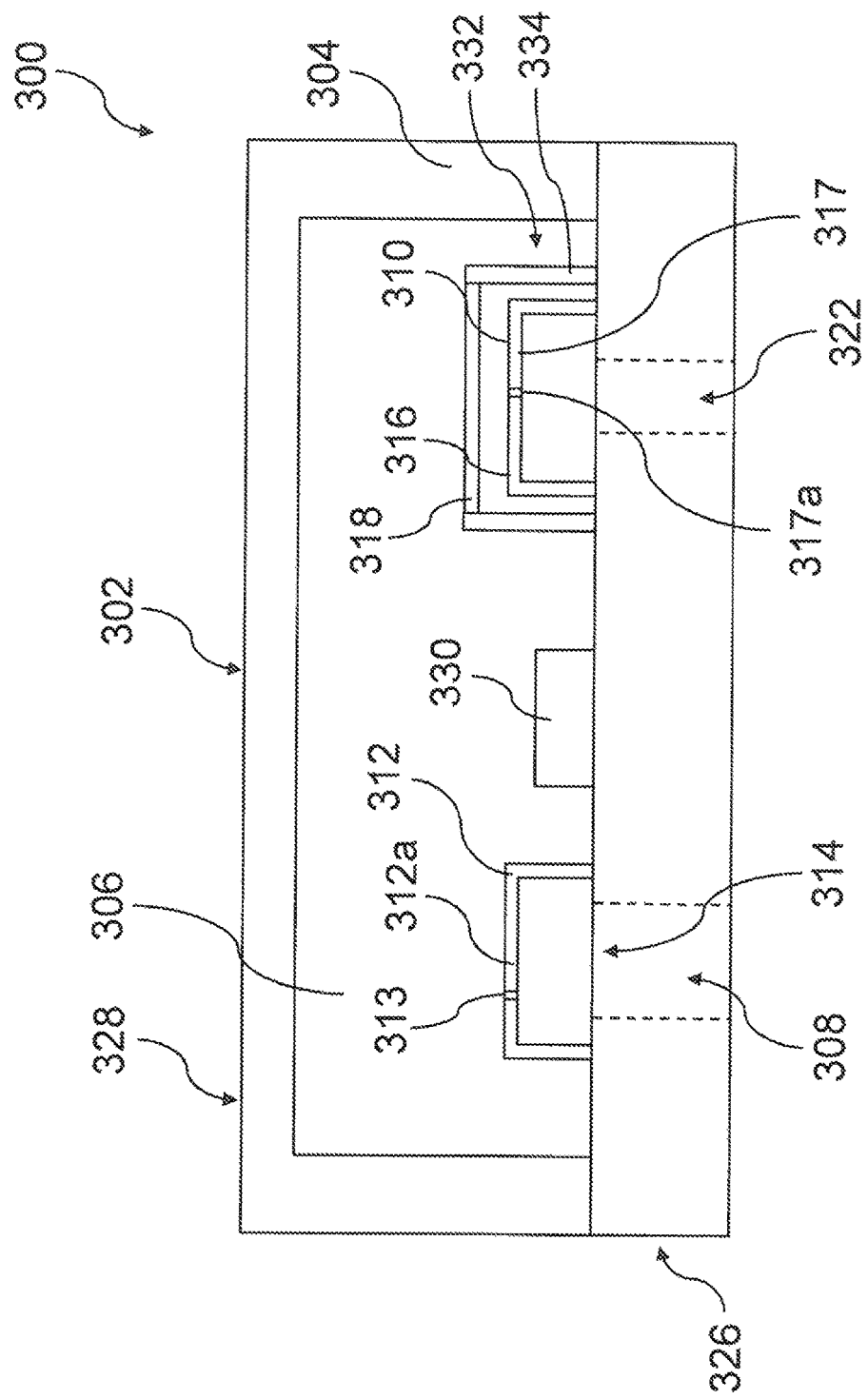
FIG. 3 shows a schematic view of another modified acoustic wave detector.

FIG. 3 shows a schematic view of another modified acoustic wave detector 300. In FIG. 3 elements corresponding to elements of the acoustic wave detector 100 shown in FIG. 1 are denoted by the same reference numerals, however enhanced by the number 200. The acoustic wave detector 300 shown in FIG. 3 will be described only inasmuch as it differs from the acoustic wave detectors 100 and 200 shown in FIG. 1 and FIG. 2.

Different from the acoustic wave detectors 100 and 200 shown in FIG. 1 and FIG. 2, the acoustic wave detector 300 shown in FIG. 3 includes a radiation unit 332 that includes a radiation unit housing 334 housing a radiation source 316, and an exit window 318 for excitation radiation generated by the radiation source 316. The exit window may be configured as an optical filter.

The radiation unit housing 334 may be formed in part of a material with a high thermal conductivity such as of a metal to efficiently dissipate heat generated by the radiation source 316 in operation. Additionally or alternatively, a heat-exchange or pressure-compensation passage 322 may be provided in the part of the exterior housing-wall 304 on which the radiation unit 332 is mounted. The heat-exchange or pressure-compensation passage 322 may be a passage between the interior of the radiation unit housing 334 and the exterior of the acoustic wave detector 300. The radiation source 316 may include an electrically heatable membrane 317 provided with a pressure-compensation hole 317a to compensate pressure differences between the individual parts of the radiation unit housing 334.

The other principles of the present invention explained above with respect to the acoustic wave detectors 100 and 200 shown in FIG. 1 and FIG. 2 apply accordingly also to the acoustic wave detector 300 shown in FIG. 3.

Figure 4:
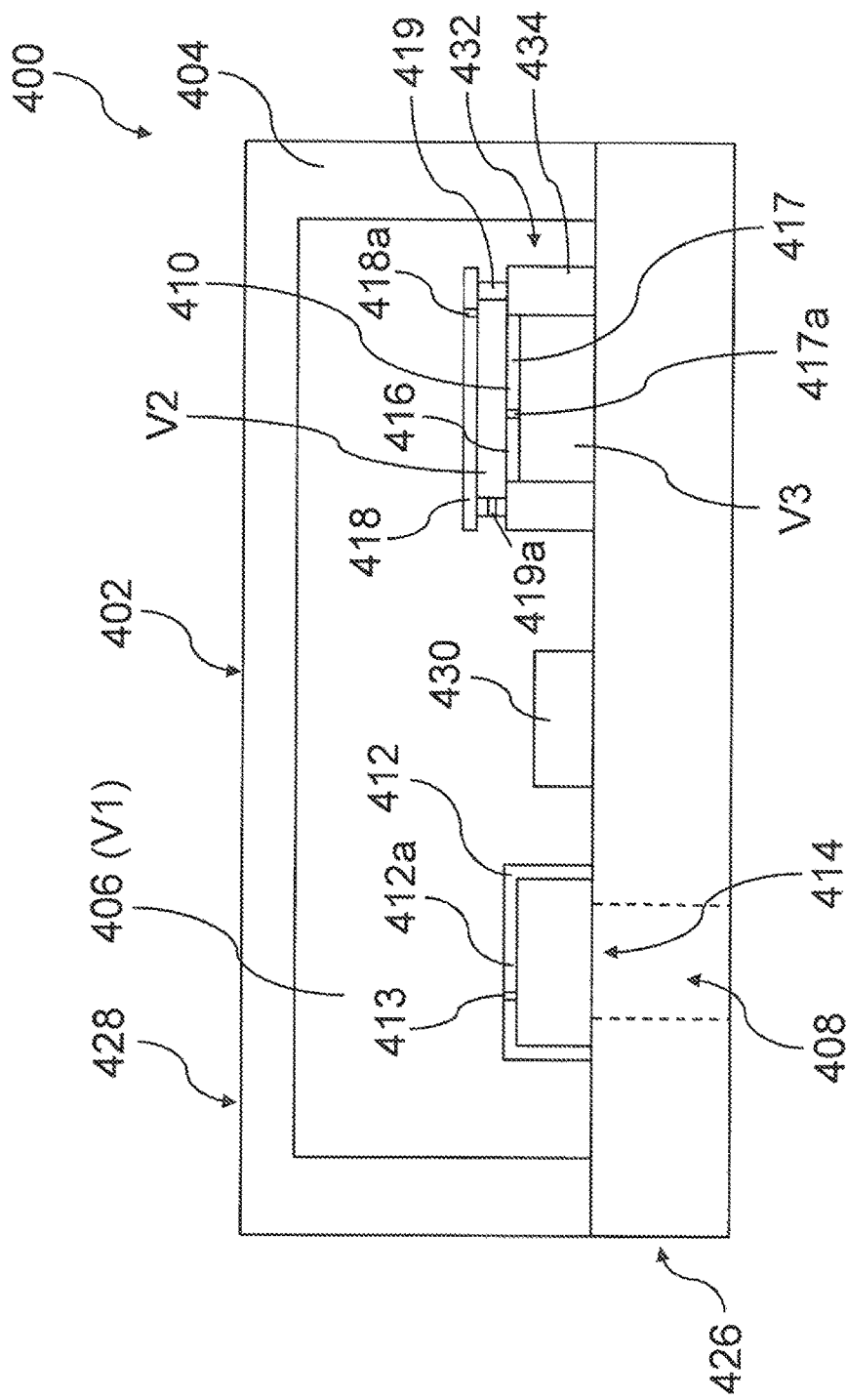
FIG. 4 shows a schematic view of yet another modified acoustic wave detector.

FIG. 4 shows a schematic view of yet another modified acoustic wave detector 400. In FIG. 4 elements corresponding to elements of the acoustic wave detector 300 shown in FIG. 3 are denoted by the same reference numerals, however enhanced by the number 100. The acoustic wave detector 400 shown in FIG. 4 will be described only inasmuch as it differs from the acoustic wave detectors 100, 200, and 300 shown in FIGS. 1 to 3.

Similar to the acoustic wave detector 300 shown in FIG. 3 the acoustic wave detector 400 shown in FIG. 4 also includes a radiation unit 432 with a radiation unit housing 434 and a radiation source 416 mounted therein. The radiation source 416 may include an electrically heatable membrane 417 provided with at least one pressure-compensation hole 417a configured to compensate pressure differences inside the radiation unit housing 434.

As shown in FIG. 4, the radiation unit 432 may include a window 418 that may be configured to provide a thermal insulation between the inside of the radiation unit housing 434 and the gas chamber 406. The window may be configured as a filter.

The radiation unit 432 may further include a coupling member 419 connecting the window 418 with the radiation unit housing 434. The coupling member 419 may be made of a thermally insulating material having a thermal conductivity of, e.g. less than 5 W/(m·K). The coupling member 419 may also provide a gastight sealing between the window 418 and the radiation unit housing 434.

As shown in FIG. 4, the window 418 and the coupling member 419 may also include heat-exchange or pressure-compensation holes 418a and 419a, respectively.

The other principles of the present invention explained above with respect to the acoustic wave detectors 100, 200 and 300 shown in FIGS. 1 to 3 apply accordingly also to the acoustic wave detector 400 shown in FIG. 4.

In the following, a simplified model of the acoustic wave detector 400 shown in FIG. 4 will be explained with reference to FIGS. 4 to 7. As indicated in FIG. 4, a plurality of chambers, including a first chamber V1, a second chamber V2, and a third chamber V3, is formed in the acoustic wave detector 400. The first chamber V1 corresponds to the gas chamber 406. The second chamber V2 is defined between the window 418 and the electrically heatable membrane 417 of the radiation source 416. The third chamber V3 is defined inside of the radiation unit housing 434.

These chambers V1, V2, V3 communicate with each other via the pressure-compensation holes 417a, 418a, and 419a. The first chamber V1 communicates with the exterior of the acoustic wave detector 400 via the opening 113 formed in the membrane 412a of the acoustic wave sensor 412. Hence, the holes 417a, 418a, and 419a and the opening 413 constitute resistances for both a gas and a heat flow between the individual chambers V1, V2, V3, and the exterior of the acoustic wave detector 400.

Figure 5:
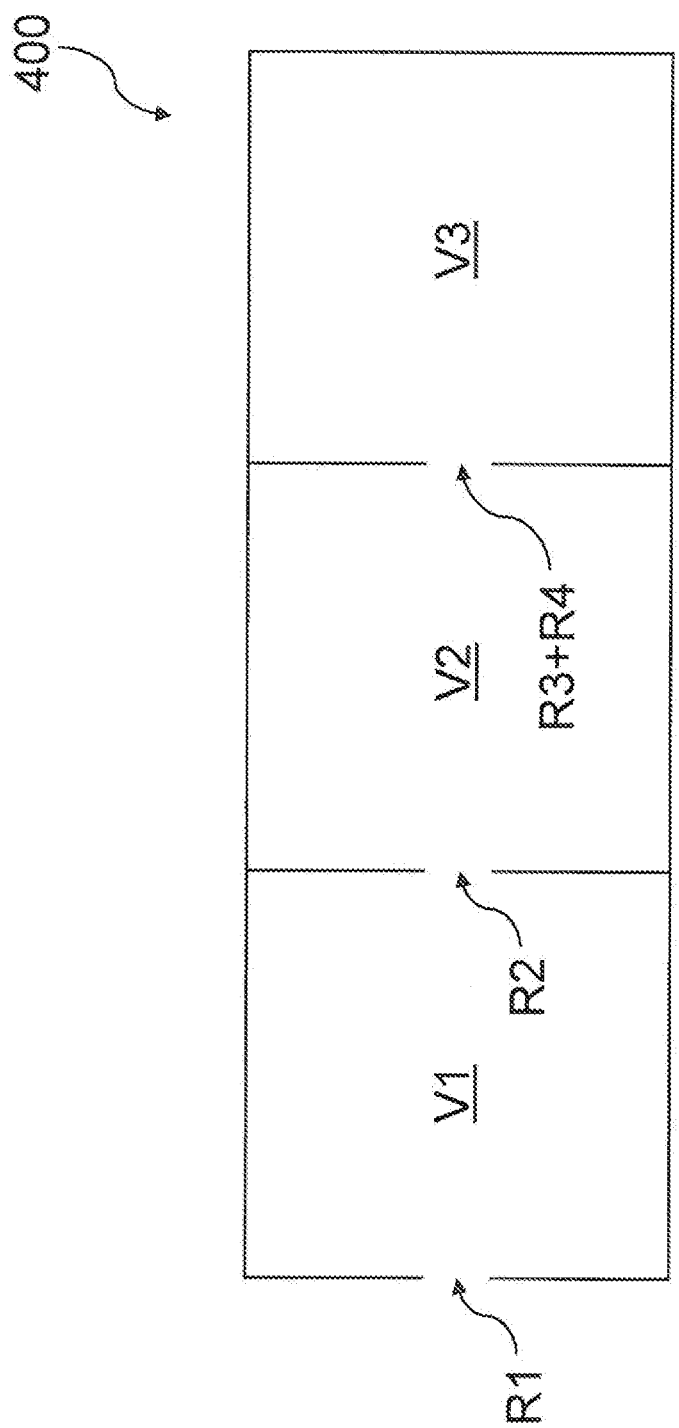
FIG. 5 shows a simplified view of the acoustic wave detector shown in FIG. 4.

The detector 400 is depicted in a simplified form in FIG. 5. In this figure, the individual chambers V1, V2, V3 of the acoustic wave detector 400 are depicted with the respective openings therebetween. As mentioned above, each of these openings constitutes a specific resistance R1 to R4.

Figure 6:
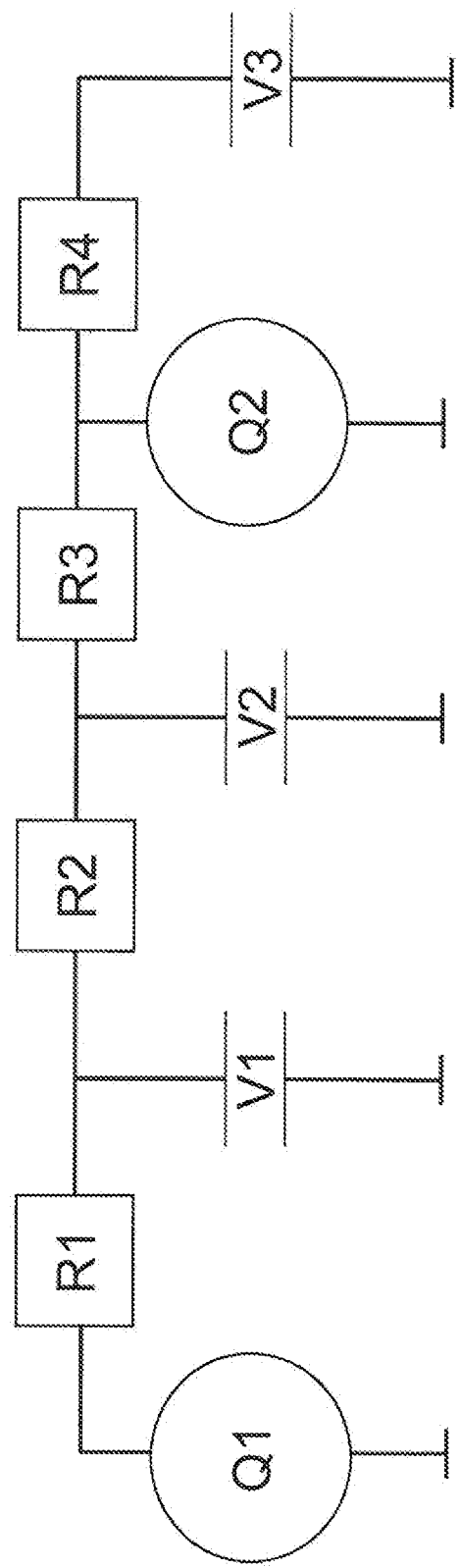
FIG. 6 shows a fluidic-acoustic equivalent model of the acoustic wave detector shown in FIGS. 4 and 5.

The effect of each of these resistances R1 to R4 as well as of the volumes of the first to third chambers V1 to V3 can be better understood with reference to FIG. 6 showing a fluidic-acoustic equivalent model of the acoustic wave detector 400 shown in FIGS. 4 and 5. The frequency dependencies of the signal components of a signal detectable by the acoustic wave sensor 412 are shown in a schematic manner in the power-vs-frequency (P-f) plot shown in FIG. 7. Each of these components can be influenced by modifying the resistances R1 to R4, the volumes of the chambers V1 to V3, and the thermal capacity of the acoustic wave detector 400.

In FIG. 6, Q1 denotes the source of the wanted signal generated by the radiation source 416 in the gas chamber 406 or input from the exterior of the acoustic wave detector 400. The frequency profile of this signal is mainly influenced by the resistance R1 of the opening 413 in the membrane 412a, by the volume of the first chamber V1, and by the thermal capacity of the acoustic wave detector 400 that basically corresponds to a system ground indicated in FIG. 6.

Figure 7:
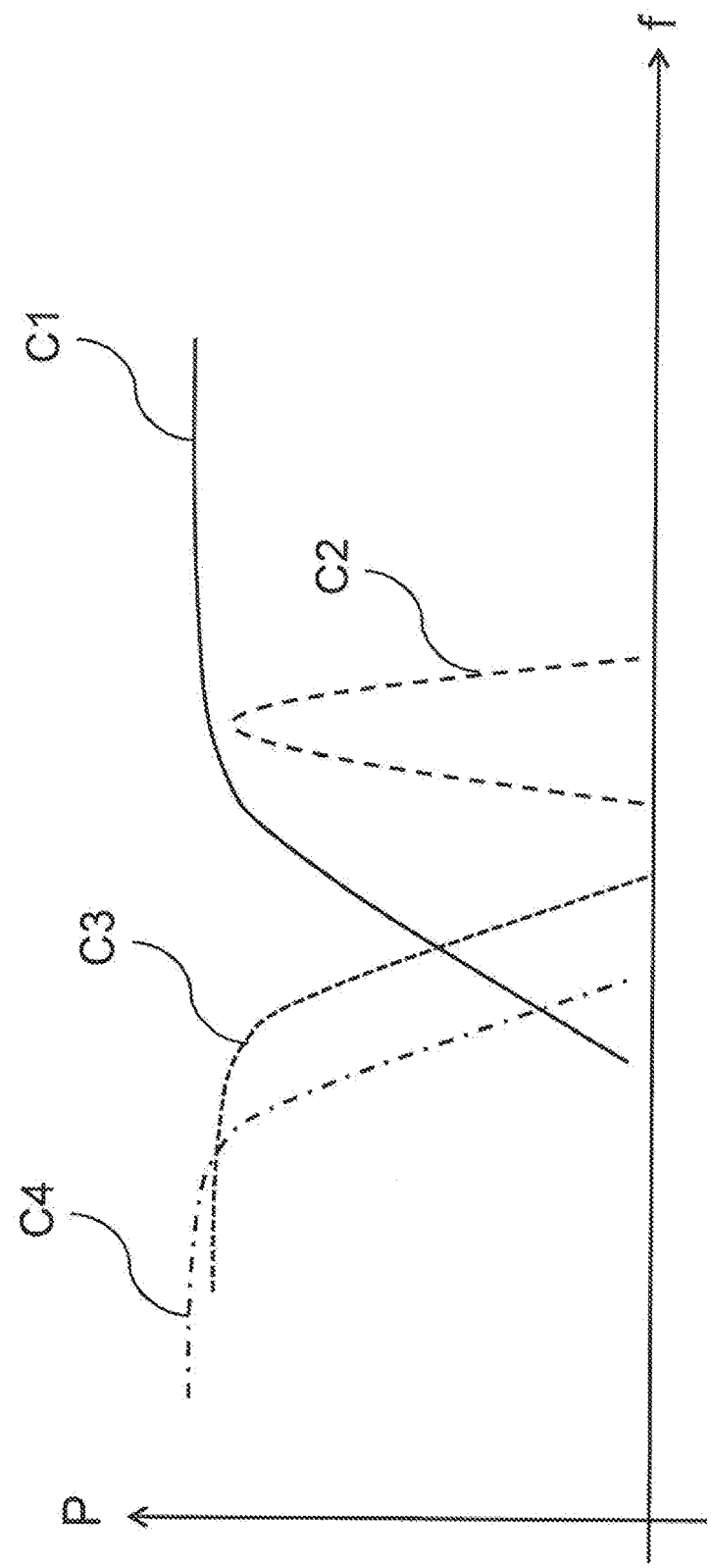
FIG. 7 shows the frequency dependency of signal components of a pressure signal detected by the acoustic wave sensor of the acoustic wave detector shown in FIGS. 4 and 5.

The frequency dependency of the wanted signal is indicated by the curve C1 in FIG. 7. As shown in this figure, the power of the wanted signal decreseases with decreasing frequencies due to the resistance R1 of the opening 413 and the volume of the first chamber V1 that act together as a low-pass filter on this signal.

In FIG. 6, Q2 denotes a signal source equivalent to the electrically heatable membrane 417. The signal generated by this source is mainly influenced by the volumes of the second and third chambers V2 and V3, as well as by the resistances R2, R3, and R4 of the holes 417a, 418a, and 419a. Here R2 takes into account the combined resistance of the holes 418a and 419a in the window 418 and the coupling member 419, respectively.

R3 and R4 denote the resistance attributable to the hole 417a formed in the electrically heatable membrane 417 with respect to the second chamber V2 and the third chamber V3, respectively.

The source Q2 has different impacts on the signal detectable by the acoustic wave sensor 412 leading to different signal components indicated by the curves C2, C3, and C4 in FIG. 7.

Firstly, the membrane 417 may act as an optical source in the first chamber V1. The signal component attributable to this effect is depicted by the curve C2 in FIG. 7. This signal component should be located at frequencies above the high pass corner frequency of the acoustic wave sensor 412, above the low pass corner frequency of the window 418, and above the thermal corner frequency of the system.

Secondly, the membrane 417 may have an influence on the signal by thermal conduction via the detector walls. More specifically, in operation of the radiation source 416, the detector walls are heated by the electrically heatable membrane 417 and conduct the heat to the first chamber V1 housing the acoustic wave sensor 412. This effect of the membrane 417 has to be suppressed, since it may overdrive the acoustic wave sensor 412. It may be suppressed by thermally decoupling the electrically heatable membrane 417 from the detector walls and by providing detector walls with a low thermal conductivity and/or a high thermal capacity. In an ideal case which is indicated in FIG. 7, the signal component C3 is located at low frequencies below the corner frequencies of the signals C1 and C2.

Thirdly, the membrane 417 may have an influence on the signal by means of acoustic waves generated outside of the first chamber V1 that subsequently propagate into the first chamber V1 through the holes 418a, 419a provided in the window 418 and the coupling member 419, respectively. The signal component attributable to this effect is indicated by the curve C4 in FIG. 7. This signal component may be shifted to low frequencies by increasing the resistance R2 of the passage between the first and second chambers V1, V2, i.e. the resistance of the holes 418a, 419a provided in the window 418 and the coupling member 419, respectively.

In the following, various aspects of this disclosure will be illustrated:

Example 1 is an acoustic wave detector. The acoustic wave detector may include an exterior housing with an exterior housing wall and a gas chamber located within the exterior housing and configured to receive a gas therein. The exterior housing wall may include an aperture providing a gas passage between the gas chamber and the exterior of the acoustic wave detector. The acoustic wave detector may further include an excitation element configured to selectively excite gas molecules of a specific type in the gas received in the gas chamber in a time-varying fashion, thereby generating acoustic waves in the gas, and an acoustic wave sensor configured to detect the acoustic waves generated in the gas and acoustic waves generated outside of the acoustic wave detector. The acoustic wave sensor may have an acoustic port overlapping with the aperture in the exterior housing wall.

In Example 2, the subject matter of Example 1 can optionally include that the excitation element includes a radiation source configured to emit radiation into the gas chamber. The radiation may be adapted to selectively excite gas molecules of a specific type in the gas in a time-varying fashion, thereby generating acoustic waves.

In Example 3, the acoustic wave detector of Example 2 can optionally include that the radiation source is configured to emit electromagnetic radiation.

In Example 4, the subject matter of Example 3 can optionally include that the radiation source is configured to emit electromagnetic radiation in the infrared and/or in the visible and/or in the ultraviolet frequency range.

In Example 5, the subject matter of Example 4 can optionally include that the radiation source includes at least one of a group consisting of: a black body, a photodiode, and a laser.

In Example 6, the subject matter of Example 5 can optionally include a black body configured as an electrically heatable membrane.

In Example 7, the subject matter of any one of Examples 2 to 6 can optionally include a window configured to transmit radiation emitted by the radiation source into the gas chamber and to thermally insulate the radiation source from the gas in the gas chamber.

In Example 8, the subject matter of Example 7 can optionally include that the window is configured as a filter adapted to selectively transmit radiation of a predetermined energy emitted by the radiation source into the gas chamber.

In Example 9, the subject matter of Example 8 can optionally include that the filter is configured as a tunable filter the transmission characteristics of which are tunable.

In Example 10, the subject matter of any one of Examples 8 or 9 can optionally include that the filter includes at least one of a plasmonic filter or a Fabry-Pérot interferometer.

In Example 11, the subject matter of any one of Examples 7 to 10 can optionally include that the window partitions the interior of the acoustic wave detector into the gas chamber and a radiation source chamber housing the radiation source.

In Example 12, the subject matter of Example 11 can optionally include that the radiation source chamber is partly delimited by the exterior housing wall of the exterior housing. The exterior housing wall may include a pressure-compensation passage between the radiation source chamber and the exterior of the acoustic wave detector.

In Example 13, the subject matter of Examples 6 and 12 can optionally include that the membrane partitions the radiation source chamber into first and second sub-chambers. The exterior housing wall may include first and second pressure-compensation passages between the first and second sub-chambers, respectively, and the exterior of the acoustic wave detector.

In Example 14, the subject matter of any one of Examples 11 to 13 can optionally include that the radiation source chamber is formed in a recess in the exterior housing wall. The recess may be covered by the window.

In Example 15, the subject matter of Example 14 can optionally include that the recess is formed in a portion of the exterior housing wall that includes a plurality of housing-wall layers.

In Example 16, the subject matter of Example 15 can optionally include that the radiation source is supported on a housing-wall layer different from an inner housing-wall layer forming part of an inner surface of the exterior housing wall.

In Example 17, the subject matter of Example 16 can optionally include that the radiation source is supported on a housing-wall layer forming part of an outer surface of the exterior housing wall.

In Example 18, the subject matter of any one of Examples 16 or 17 can optionally include that the housing-wall layer on which the radiation source is supported has a lower thermal conductivity than the inner housing-wall layer.

In Example 19, the subject matter of any one of Examples 7 to 18 can optionally further include a radiation unit that includes an radiation unit housing, the radiation source housed within the radiation unit housing, and the window forming an exit window of the radiation unit housing.

In Example 20, the subject matter of any one of Examples 1 to 19 can optionally include that the acoustic wave sensor is located inside the exterior housing.

In Example 21, the subject matter of any one of Examples 1 to 20 can optionally include that the acoustic wave sensor includes a membrane displaceable by the acoustic waves to be detected. A displacement of the membrane may be indicative of characteristics of the acoustic waves to be detected.

In Example 22, the subject matter of Example 21 can optionally include that the membrane is located within the gas chamber.

In Example 23, the subject matter of Example 22 can optionally include that the acoustic wave sensor is located within the gas chamber.

In Example 24, the subject matter of any one of Examples 21 to 23 can optionally include that the membrane delimits the gas chamber and includes at least one opening formed therethrough. The at least one opening may provide a gas inlet and/or a gas outlet of the gas chamber.

In Example 25, the subject matter of any one of Examples 1 to 24 can optionally include that the acoustic wave sensor is configured as a microphone.

In Example 26, the subject matter of Example 25 can optionally include that the acoustic wave sensor is configured as a microphone of a mobile phone. The gas chamber may be located in the backvolume of the microphone.

In Example 27, the subject matter of any one of Examples 1 to 26 can optionally include that the gas chamber has a volume in the range from about 1 to about 10 mm$^3$.

In Example 28, the subject matter of any one of Examples 1 to 27 can optionally include that the exterior housing includes a substrate and a lid defining the gas chamber therebetween.

In Example 29, the subject matter of Example 28 can optionally include that the acoustic wave sensor and/or the excitation element are mounted on the substrate.

In Example 30, the subject matter of any one of Examples 28 or 29 can optionally include an electronic component mounted on the substrate configured to process signals output from the acoustic wave sensor and/or configured to control the excitation element.

In Example 31, the subject matter of any one of Examples 1 to 30 can optionally include that the gas chamber is delimited by a reflector.

In Example 32, the subject matter of Example 31 can optionally include that the reflector has a reflectance in the infrared and/or in the visible and/or in the ultraviolet frequency range of at least 20% or of at least 50% or even of at least 80%.

In Example 33, the subject matter of any one of Examples 28 to 30 and any one of claim 31 or 32 can optionally include that the substrate and/or the lid are configured as reflectors.

Example 34 is a mobile device, including an acoustic wave detector of any one of Examples 1 to 33.

In Example 35, the subject matter of Example 34 includes that the mobile device is configured as a mobile phone.

Example 36 is a microphone device. The microphone device may include a microphone configured to detect acoustic waves, and a radiation source positioned inside a backvolume of the microphone and configured to emit modulated radiation adapted to excite a gas in the backvolume of the microphone, thereby generating acoustic waves detectable by the microphone.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:
1. An acoustic wave detector, comprising:
an exterior housing with an exterior housing wall;
a gas chamber located within the exterior housing and configured to receive a gas therein, wherein the exterior housing wall comprises an aperture providing a gas passage between the gas chamber and an exterior of the acoustic wave detector;
an excitation element configured to selectively excite gas molecules of a specific type in the gas received in the gas chamber in a time-varying fashion, thereby generating acoustic waves in the gas; and
an acoustic wave sensor configured to detect the acoustic waves generated in the gas and acoustic waves generated outside of the acoustic wave detector, wherein the acoustic wave sensor has an acoustic port overlapping with the aperture in the exterior housing wall.

2. The acoustic wave detector of claim 1, wherein the excitation element comprises a radiation source configured to emit radiation into the gas chamber, wherein the radiation is adapted to selectively excite gas molecules of a specific type in the gas in a time-varying fashion, thereby generating acoustic waves.

3. The acoustic wave detector of claim 2, wherein the radiation source is configured to emit electromagnetic radiation.

4. The acoustic wave detector of claim 3, wherein the radiation source is configured to emit electromagnetic radiation in the infrared and/or in the visible and/or in the ultraviolet frequency range.

5. The acoustic wave detector of claim 2, further comprising: a window configured to transmit radiation emitted by the radiation source into the gas chamber and to thermally insulate the radiation source from the gas in the gas chamber.

6. The acoustic wave detector of claim 5, wherein the window is configured as a filter adapted to selectively transmit radiation of a predetermined energy emitted by the radiation source into the gas chamber.

7. The acoustic wave detector of claim 6, wherein the filter is configured as a tunable filter, the transmission characteristics of which are tunable.

8. The acoustic wave detector of claim 5, wherein the window partitions the interior of the acoustic wave detector into the gas chamber and a radiation source chamber housing the radiation source.

9. The acoustic wave detector of claim 8, wherein the radiation source chamber is formed in a recess in the exterior housing wall, wherein the recess is covered by the window.

10. The acoustic wave detector of claim 9, wherein the recess is formed in a portion of the exterior housing wall that comprises a plurality of housing-wall layers.

11. The acoustic wave detector of claim 10, wherein the radiation source is supported on a housing-wall layer different from an inner housing-wall layer forming part of an inner surface of the exterior housing wall.

12. The acoustic wave detector of claim 9, wherein the recess is enclosed by the window and the exterior housing wall.

13. The acoustic wave detector of claim 9, wherein the window is disposed on at least a portion of an inner surface of the exterior housing wall.

14. The acoustic wave detector of claim 5, further comprising: a radiation unit that comprises a radiation unit housing, the radiation source housed within the radiation unit housing, and the window forming an exit window of the radiation unit housing.

15. The acoustic wave detector of claim 1, wherein the acoustic wave sensor is located inside the exterior housing.

16. The acoustic wave detector of claim 1, wherein the acoustic wave sensor comprises a membrane displaceable by the acoustic waves to be detected, wherein a displacement of the membrane is indicative of characteristics of the acoustic waves to be detected.

17. The acoustic wave detector of claim 16, wherein the membrane is located within the gas chamber.

18. The acoustic wave detector of claim 17, wherein the acoustic wave sensor is located within the gas chamber.

19. The acoustic wave detector of claim 16, wherein the membrane delimits the gas chamber and comprises at least one opening formed therethrough, wherein the at least one opening provides a gas inlet and/or a gas outlet of the gas chamber.

20. The acoustic wave detector of claim 1, wherein the acoustic wave sensor is configured as a microphone.

21. The acoustic wave detector of claim 1, wherein the gas chamber has a volume in the range from about 1 to about 10 $mm^3$.

22. The acoustic wave detector of claim 1, wherein the exterior housing comprises a substrate and a lid defining the gas chamber therebetween.

23. The acoustic wave detector of claim 1, wherein the gas chamber is delimited by a reflector.

* * * * *